United States Patent [19]

Ishiguro et al.

[11] 4,091,220
[45] May 23, 1978

[54] MORPHOLINOCARBONYL ALKYL N-BENZYLPIPERAZINES

[75] Inventors: Toshihiro Ishiguro; Yasushi Sanno, both of Osaka, Japan

[73] Assignee: Takeda Chemical Industries, Ltd., Osaka, Japan

[21] Appl. No.: 793,356

[22] Filed: May 3, 1977

Related U.S. Application Data

[63] Continuation-in-part of Ser. No. 633,546, Nov. 19, 1975, abandoned.

[30] Foreign Application Priority Data

Nov. 19, 1974    Japan ................................. 49-133281

[51] Int. Cl.$^2$ ............................................ C07D 413/02
[52] U.S. Cl. .................................... 544/121; 542/470;
424/248.54; 424/248.56; 424/250; 544/365;
544/402; 544/400; 544/391; 544/401; 544/390
[58] Field of Search .......................................... 544/121

[56] References Cited

PUBLICATIONS

Ishiguro et al., "Chem Abstracts" vol. 85, (1976) No. 94405r.

*Primary Examiner*—Henry R. Jiles
*Assistant Examiner*—R. W. Ramsuer
*Attorney, Agent, or Firm*—Wenderoth, Lind & Ponack

[57] ABSTRACT

Novel N-benzylpiperazine derivatives of the general formula

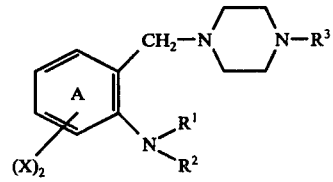

wherein $R^1$ and $R^2$ are same or different and each stands for a hydrogen atom or an acyl group; $R^3$ stands for a hydrogen atom; a carbamoyl group, an acyl group which is unsubstituted or substituted by mercapto or morpholino, or an alkyl group which is unsubstituted or substituted by hydroxy, aryl or aminocarbonyl represented by the formula

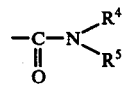

wherein each of $R^4$ and $R^5$ is a hydrogen atom, a lower alkyl group having 1 to 3 carbon atoms or a cyclohexyl group, or $R^4$ and $R^5$ form a morpholino or piperidino ring together with the nitrogen atom adjacent thereto, and X stands for a halogen atom, and pharmaceutically acceptable acid addition salts thereof. These compounds and salts thereof have respiratory tract fluid secretion stimulatory properties and are useful as medicines such as respiratory track fluid secretion stimulators.

10 Claims, No Drawings

MORPHOLINOCARBONYL ALKYL N-BENZYLPIPERAZINES

This application is a continuation-in-part of Ser. No. 633,546, filed Nov. 19, 1975, now abandoned.

The present invention relates to novel N-benzylpiperazine derivatives useful as medicines, which are represented by the general formula (I)

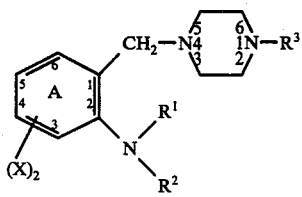

wherein $R^1$ and $R_2$ are the same or different and each stands for a hydrogen atom or an acyl group; $R^3$ stands for a hydrogen atom, a carbamoyl group, an acyl group which is unsubstituted or substituted by mercapto or morpholino, or an alkyl group which is unsubstituted or substituted by hydroxy, aryl or aminocarbonyl represented by the formula

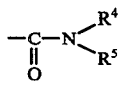

wherein each of $R^4$ and $R^5$ is a hydrogen atom, a lower alkyl group having 1 to 3 carbon atoms or a cyclohexyl group, or $R^4$ and $R^5$ form a morpholino or piperidino ring together with the nitrogen atom adjacent thereto, and X stands for a halogen atom, and pharmaceutically acceptable acid addition salts thereof, and also relates to a process for producing the same.

The compounds (I) and their pharmaceutically acceptable acid addition salts have respiratory tract fluid secretion stimulatory, antihistaminic and/or anticonvulsive properties and, accordingly, are of use as medicines such as respiratory tract fluid secretion stimulators, i.e. expectorants, antihistaminics, anticonvulsants and so on.

Referring to each of the above formulas, the acyl groups designated by $R^1$ and $R^2$ are exemplified by alkylcarbonyl groups whose alkyl moieties are lower alkyls having 1 to 3 carbon atoms such as acetyl, propionyl, butylyl, etc. or arylcarbonyl groups such as benzoyl, etc. As the acyl group designated by $R^3$, there may be mentioned the same alkylcarbonyl groups, whose alkyl moieties are lower alkyls having 1 to 3 carbon atoms, or arylcarbonyl groups as those designated by $R^1$ and $R^2$ (e.g. acetyl, propionyl, butylyl, benzoyl). Where the acyl group designated by $R^3$ is further substituted by mercapto or morpholino, one or more such substituents may occur in optional positions on the acyl group $R^3$. As such substituted acyl group, the acyl substituted by one substituent is preferred. As examples of such substituted acyl groups, there may be mentioned such mercaptoacyl groups as mercaptoacetyl, β-mercaptopropionyl, etc., morpholinoacetyl, β-morpholinopropionyl and so on. As the alkyl groups designated by $R^3$, there may be mentioned saturated and unsaturated, straight-chain or branched alkyl groups having 1 to 6 carbon atoms, such as methyl, ethyl, propyl, isopropyl, butyl, isobutyl, tert-butyl, sec-butyl, allyl, pentyl, hexyl and so on. Among the alkyl groups, lower alkyl group having 1 to 3 carbon atoms is preferred. The lower alkyl groups designated by $R^4$ and $R^5$ are exemplified by methyl, ethyl, propyl, isopropyl. As examples of the aminocarbonyl group of the formula

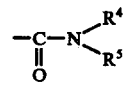

there may be mentioned carbamoyl, dimethylaminocarbonyl, diethylaminocarbonyl, dipropylaminocarbonyl, N-methylaminocarbonyl, N-ethylaminocarbonyl, N-n-propylaminocarbonyl, N-isopropylaminocarbonyl, N-methyl-N-cyclohexylaminocarbonyl, N-ethyl-N-cyclohexylaminocarbonyl, morpholinocarbonyl, piperidinocarbonyl and so on.

Where such an alkyl group designated by $R^3$ is substituted by hydroxy, aryl or such aminocarbonyl, one or more such substituents may occur in optional positions on the alkyl group. As such substituted alkyl, the alkyl substituted by one substituent is preferred. When the substituent on the alkyl group designated by $R^3$ is an aryl group, the aryl group may for example be phenyl. As such phenyl-substituted alkyls, there may for example be mentioned benzyl, phenethyl and other aralkyl groups. Where the alkyl group designated by $R^3$ is substituted by hydroxy, the substituted alkyl may for example be hydroxymethyl, β-hydroxyethyl γ-hydroxypropyl or other hydroxyalkyl. And where the alkyl group designated by $R^3$ is substituted by the aminocarbonyl of the above formula, the substituted alkyl may for example be carbamoylmethyl, morpholinocarbonylmethyl, piperidinocarbonylmethyl, dimethylaminocarbonylmethyl, diethylaminocarbonylmethyl, isopropylaminocarbonyl methyl, N-methyl-N-isopropylaminocarbonylmethyl, N-methyl-N-cyclohexylaminocarbonylmethyl and so on. As the substituent at $N_1$-position of the general formula (I), which is designated by $R^3$, the alkyl or such substituted alkyl group is preferred. The halogen atom designated by X is a chlorine, bromine, iodine or fluorine atom, although bromine or chlorine atom is particularly preferred. And as the positions of tha halogen atoms, 3- and 5-positions of the ring A of the general formula (I) is particularly preferred.

In one aspect the invention provides compounds of the formula

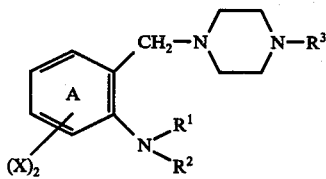

wherein $R^1$ and $R^2$ are the same or different and each stands for a hydrogen atom, alkylcarbonyl, whose alkyl moiety is of 1 to 3 carbon atoms, or benzoyl; $R^3$ stands for straight-chain or branched alkyl having 1 to 6 carbon atoms which is substituted by amino-carbonyl represented by the formula

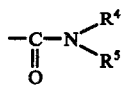

wherein $R^4$ and $R^5$ form a morpholino ring together with the nitrogen atom adjacent thereto, and X stands for a halogen atom, and a pharmaceutically acceptable acid addition salt thereof.

In a further aspect the invention provides compounds of the formula

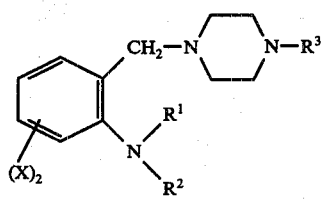

wherein $R^1$ and $R^2$ are the same or different and each stands for a hydrogen atom, alkylcarbony, whose alkyl moiety is of 1 to 3 carbon atoms, or benzoyl; $R^3$ stands for alkylcarbonyl, whose alkyl moiety is of 1 to 3 carbon atoms, which is substituted by mercapto, and X stands for a halogen atom, and pharmaceutically acceptable acid addition salt thereof.

The compounds (I) are produced by reacting a compound of the general formula (II)

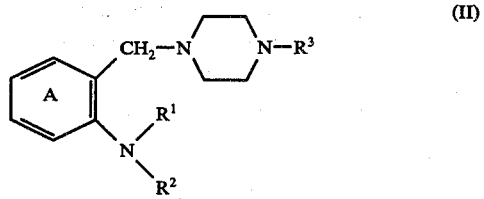

wherein $R^1$, $R^2$ and $R^3$ have the same meanings as defined hereinbefore, with a halogenating agent. As the halogenating agent, use may be made of any reagent useful for the halogenation of aromatic rings, such as halogens per se, e.g. chlorine and bromine, bromochloride ($Br^+ Cl^-$) which is obtainable from sodium bromide and chlorine, and chlorobromide ($Cl^+ Br^-$) which can be prepared from sodium chloride and bromine. This reaction is normally conducted in an inert solvent.

As examples of the inert solvent for this reaction, there may be mentioned aromatic hydrocarbons such as benzene, toluene, etc.; petroleum benzin, n-hexane, etc.; halogenated hydrocarbons such as carbon tetrachloride, chloroform, dichloromethane, etc.; and organic carboxylic acids such as acetic acid, propionic acid and so on.

Of these reaction solvents, organic carboxylic acids and halogenated hydrocarbons are the most advantageous.

The reaction temperature may normally be within the range of about −20° to about 140° C, although the reaction may be conducted with advantage at room temperature. While the proportion of said halogenating agent is normally about 2 to about 20 molar equivalents, it is preferable to employ 2 molar equivalents or slightly more of the halogenating agent to each mole of compound (II).

The object compounds (I) are produced in the free form or in the form of salt of hydrogen halide corresponding to the halogenating agent employed and, in whichever of the cases, may be purified by conventional procedures such as chromatography, distillation, recrystallization and so on. When the object compounds (I) thus obtained are in the form of the free base, they can be converted to an acid addition salt by a conventional procedure using a pharmaceutically acceptable inorganic or organic acid, for example by reacting 1 to 3 molar equivalents of compound (I) with an alcoholic solution of each equivalent of such acid. As the aforesaid acid, there may be mentioned such inorganic acids as hydrochloric acid, hydrobromic acid, sulfuric acid, phosphoric acid, etc. and such organic acids as lactic acid, citric acid, tartaric acid, maleic acid and so on.

The contemplated compounds (I) may also be produced by the synthetic processes illustrated below in formulas.

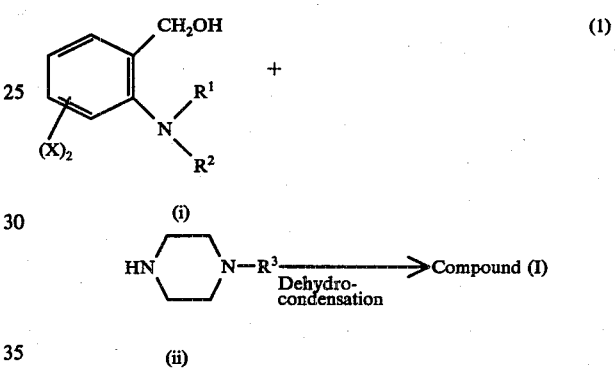

wherein $R^1$, $R^2$, $R^3$ and X have the same meanings as defined hereinbefore.

The dehydration reaction in this process is conducted in the presence of a fatty acid, particularly in the presence of acetic acid, propionic acid, valeric acid or the like, and in the absence or presence of a solvent, which may for example be xylene or tetralin. The proportion of Compound (ii) is normally about 2 to 20 molar equivalent to mole of Compound (i). The compounds (I) may be produced by heating the above mixture at 120° to 200° C.

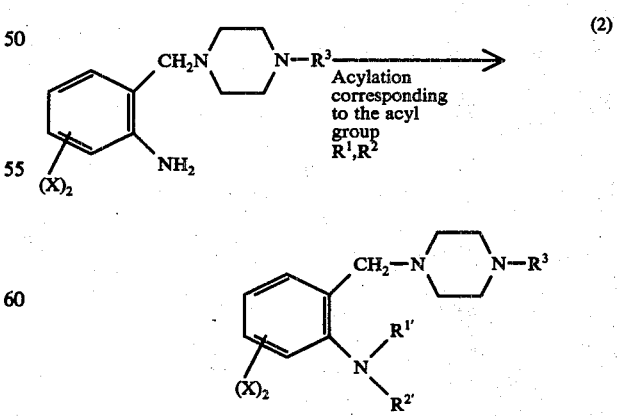

wherein $R^1$, $R^2$, $R^3$ and X have the same meanings as defined hereinbefore; $R^{1'}$ and $R^{2'}$ are the same acyl groups as those mentioned for $R^1$ and $R^2$.

The acylation reaction of this step is carried out under the same conditions as those of the acylation reaction of compound (II') in step (B) for the production of the starting compound (II) of this invention which will hereinafter be described.

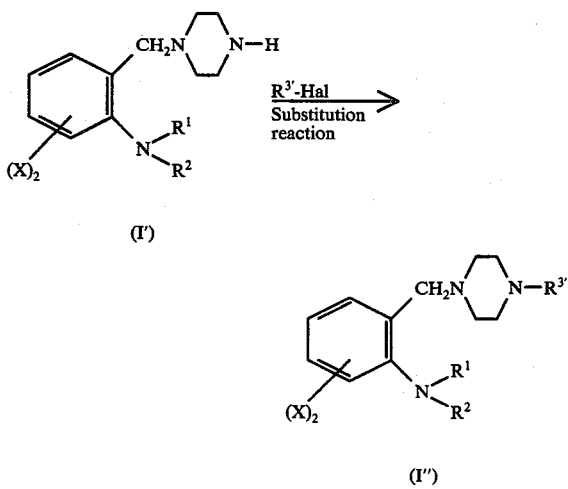

wherein $R^1$, $R^2$ and X have the same meanings as defined hereinbefore; Hal stands for a halogen atom such as chlorine, bromine or the like; $R^{3'}$ stands for $R^3$ except a hydrogen atom.

The substitution reaction of this process comprises reacting a halide represented by $R^{3'}$—Hal with the starting compound (I') to obtain (I''). The halide $R^{3'}$—Hal may be produced according to the method described in Il Farmaco Edizione Scientifica 18, 828(1963), or a method similar thereto. As the solvent, there may be mentioned alcohols (e.g. methanol, ethanol), ketones (e.g. acetone, methyl ethyl ketone), hydrocarbons (e.g. benzene, toluene), halogenated hydrocarbons (e.g. chloroform, dichloromethane), dimethylformamide and so on. The reaction temperature is within the range of 0° to 120° C. $R^{3'}$—Hal is normally used in a proportion of one molar equivalent based on compound (I') or a slight excess over compound (I').

The object compounds (I) or salts thereof which are produced by the methods described hereinbefore are novel compounds possessing respiratory tract fluid secretion stimulatory, antihistaminic and/or anticonvulsive properties and, accordingly, these compounds are useful, for example, for aiding in the expulsion of mucus or exudate from the bronchi and trachea of mammals, including e.g. rabbit, which are suffering from bronchitis. Thus, they are of use as medicines such as respiratory tract fluid secretion stimulators i.e. expectorants, antihistaminics, anticonvulsants and so on.

In using the compounds (I) or the salts thereof as medicines mentioned above, they may be administered orally or parenterally in admixture with a pharmaceutically acceptable diluent, vehicle, excipient or/and solvent and in such dosage forms as tablets, capsules, powders, granules, solutions, syrups, aerosols, injections, suppositories and so on.

Of the above compounds and salts, acid addition salts of compound (I) are soluble in water and particularly suited for use as injections, aqueous solutions and so on. While the dosage of said compounds (I) or salts thereof depends upon the disease to be dealt with and the particular species of compound or salt, among other variables, the ordinary dosage level per adult human in the above medical applications is in the range of about 5 to 200 milligrams daily.

The starting compounds (II) of this invention may be produced according to the method described in Journal of Chemical Society, 1722(1968), or a method similar thereto, i.e. by the process shown below in formulas.

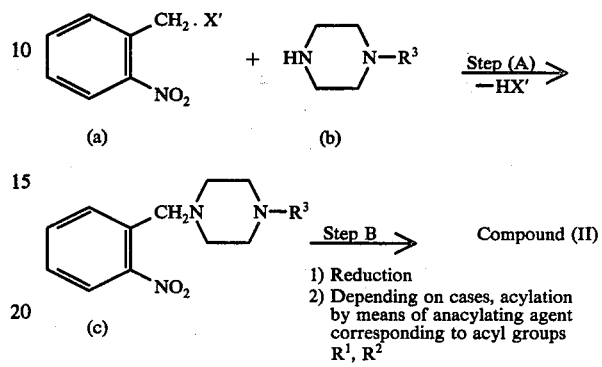

wherein $R^1$, $R^2$ and $R^3$ have the same meanings as defined above; X' stands for the same halogen atom as represented by X.

The reaction in step (A) comprises reacting compound (a) with compound (b). The compound (b) may be produced according to the method described in Journal of Chemical Society, 39(1929), or a method similar thereto. The proportion of compound (b) is usually about 1 to 3 molar equivalents per mole of compound (a). This reaction is normally conducted in a solvent which may, for example, be an alcohol (e.g. methanol, ethanol, propanol, etc.), a halogenated hydrocarbon (e.g. carbon tetrachloride, chloroform, dichloromethane, etc.), a ketone (e.g. acetone, methyl ethyl ketone, etc.), dimethylformamide or the like. The reaction temperature may normally be within the range of 0° to 120° C, although when a solvent is employed, the reaction may be carried out with advantage in the neighborhood of the boiling point of the solvent.

The reaction in step (B) comprises the reduction of the compound (c) obtained by step (A). The reducing agent may be any agent that is able to reduce a nitro group on an aromatic ring to an amino group. Thus, for example, there may be mentioned catalytic reduction in the presence of a catalyst such as Raney nickel, platinum oxide or palladiumcarbon or the like; reduction by means of sodium hydrosulfide; reduction by means of Raney nickel and hydrazine hydrate. The conditions of reduction depends upon the type of reducing agent employed. In the case of catalytic reduction, the reaction normally proceeds at room temperature. The reduction by means of sodium hydrosulfide is carried out near the boiling point of the solvent employed, e.g. an alcohol (methanol, ethanol, propanol or the like). While the reaction by means of Raney nickel-hydrazine hydrate is carried out in the presence of a solvent such as the alcohol mentioned above, it need not be conducted under heating because the reaction per se is an exothermic reaction. Preferably, this reaction is carried out within the temperature range of about 50° to 70° C.

In the general formula (II), the compound (II'') in which $R^1$ and/or $R^2$ is an acyl group is produced by the acylation of the amino group at 2-position of an 2-aminobenzylpiperazine derivative (II') which is obtainable by the reduction of step (B) described hereinbefore.

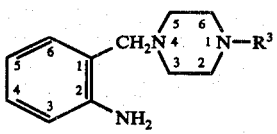

(II')

wherein $R^3$ has the same meaning as defined above.

This acylation is carried out by reacting an 2-aminobenzylpiperazine derivative (II') with an acylating agent. As this acylating agent, there may be mentioned reactive derivatives of the lower aliphatic or aromatic carboxylic acids corresponding to the acyl groups $R^1$ and $R^2$ (such as acid halides, e.g. acetyl chloride, benzoyl chloride, etc.; acid anhydrides, e.g. acetic anhydride, benzoic anhydride, etc.; and mixed acid anhydrides of such acids). The proportion of acylating agent is normally about 1 to 4 molar equivalents per mole of compound (II'). This reaction is normally conducted in a solvent which may, for example, be am ester e.g. ethyl acetate or butyl acetate or an ether, e.g. tetrahydrofuran or dioxane. The reaction temperature is normally within the range of about 0° to about 120° C. In acylation of compound (II') wherein $R^3$ is hydrogen, acyl groups may be introduced not only to the amino group at 2-position but also to $N_1$-position of the formula (II'). The resultant 2-(monoacylamino)- or 2-(diacylamino)benzylpiperazine derivative (II'') may, if desired, be deacylated as to the acyl moiety or moieties of the mono or di-acylamino group by a conventional procedure, for example by hydrolysis with a mineral acid such as hydrochloric acid, sulfuric acid or phosphoric acid.

Conversely, the 2-(monoacylamino)-benzylpiperazine derivative (II') may be further subjected to the aforesaid acylation reaction to obtain the 2-(diacylamino)-benzylpiperazine derivative (II'').

The following Reference Examples and Examples are further illustrative of this invention, wherein the term "part(s)" means "weight part(s)" unless otherwise specified, and the relationship between "part(s)" and "volume part(s)" corresponds to that between gram(s) and milliliter(s).

REFERENCE EXAMPLE 1

(1) Production of $N_1$-methyl-$N_4$-(2-nitrobenzyl)piperazine

In 20 volume parts of ethanol is dissolved 2.16 parts of o-nitrobenzyl chloride, followed by the addition of 1.02 parts of N-methyl piperazine and 1.3 parts of potassium carbonate. The mixture is reacted under reflux for 1 hour. The reaction mixture is then filtered and the solvent is removed from the filtrate by distillation under reduced pressure. The residue is extracted with water-ether (1:1). The ethereal layer is taken and dried over anhydrous sodium sulfate and the solvent is then distilled off. This procedure gives $N_1$-methyl-$N_4$-(2-nitrobenzyl)piperazine as a brown colored oily substance. Infrared absorption spectrum (liquid film)cm$^{-1}$: 1610, 1538.

Nuclear magnetic resonance spectrum (NMR) [in deuteriochloroform (CDCl$_3$)] ppm: 2.25(3H, singlet), 2.40(4H, singlet), 3.73(2H, singlet), 7.2 to 7.9(4H, multiplet)

(2) Production of $N_1$-methyl-$N_4$-(2-aminobenzyl)piperazine

In 30 volume parts of ethanol is dissolved 1.87 parts of $N_1$-methyl-$N_4$-(2-nitrobenzyl)piperazine, followed by the addition of 3.0 parts of Raney nickel. Then, 3.0 parts of hydrazine hydrate is further added to the mixture and the entire mixture is kept at room temperature for 2 hours. Following this reaction, the Raney nickel is filtered off and the solvent is distilled off under reduced pressure. The residual oily substance is recrystallized from aqueous methanol. The procedure gives pale yellow crystals melting at 78° to 79° C.

Elemental analysis: Calculated for $C_{12}H_{19}N_3$: C, 70.20; H, 9.33; N, 20.47. Found: C, 70.01; H, 9.69; N, 20.40.

According to a similar manner to that of Reference Example 1, the following compounds are obtained;

$N_1$-hydro-$N_4$-(2-aminobenzyl)piperazine (melting point: 127° to 128° C); $N_1$-n-propyl-$N_4$-(2-aminobenzyl)piperazine hydrochloride (melting point: 215° to 220° C); $N_1$-benzyl-$N_4$-(2-aminobenzyl)piperazine (melting point: 92° to 93° C); $N_1$-(morpholinocarbonylmethyl)-$N_4$-(2-aminobenzyl)piperazine (melting point: 158° to 160° C); $N_1$-β-hydroxyethyl)-$N_4$-(2-aminobenzyl) piperazine maleate (melting point: 152° to 153° C); $N_1$-cinnamyl-$N_4$-(2-aminobenzyl) piperazine (melting point: 185° to 187° C); $N_1$-isopropyl-$N_4$-(2-aminobenzyl)piperazine, oily substance, NMR (in CDCl$_3$) ppm: 1.03(6H, doublet, J=7), 2.50(8H, singlet), 2.88(1H, doublet, J=7), 3.46(2H, singlet), 6.4 to 7.2 (4H, multiplet); $N_1$-(morpholinomethylcarbonyl)-$N_4$-(2-aminobenzyl)piperazine, oily substance, NMR(in CDCl$_3$) ppm: 2.3 to 2.8 (8H, multiplet), 3.20(2H, singlet), 3.43(2H, singlet), 3.4 to 3.9(8H, multiplet), 5.0(2H), 6.4 to 7.2 (4H, multiplet); $N_1$-(mercaptomethylcarbonyl)-$N_4$-(2-aminobenzyl)piperazine, amorphous, NMR(in CDCl$_3$) ppm: 2.1 to 2.7(4H, multiplet), 3.3 to 3.9(4H, multiplet), 3.43(2H, singlet), 3.50(2H, singlet), 6.5 to 7.4(4H, multiplet); $N_1$-(aminocarbonylmethyl)-$N_4$-(2-aminobenzyl)piperazine (melting point: 131° to 132° C); $N_1$-(diethylaminocarbonylmethyl)-$N_4$-(2-aminobenzyl)piperazine (melting point: 91° to 92° C); $N_1$-(piperidinocarbonylmethyl)-$N_4$-(2-aminobenzyl)piperazine (melting point: 140° to 141° C); $N_1$-(N-isopropylaminocarbonylmethyl)-$N_4$-(2-aminobenzyl)piperazine (melting point: 148° to 149° C); $N_1$-(N-methyl-N-cyclohexylaminocarbonylmethyl)-$N_4$-(2-aminobenzyl)piperazine hydrochloride (melting point: 164° to 166° C); $N_1$-aminocarbonyl-$N_4$-(2-aminobenzyl)-piperazine (melting point: 175° to 177° C); $N_1$-(molpholinocarbonylethyl)-$N_4$-(2-aminobenzyl)-piperazine (melting point: 65° to 67° C).

REFERENCE EXAMPLE 2

(1) Production of $N_1$-(morpholinocarbonylmethyl)-$N_4$-(2-monobenzoylaminobenzyl)piperazine To a solution of 0.1 part of $N_1$-(morpholinocarbonylmethyl)-$N_4$-(2-aminobenzyl)piperazine in 3 volume parts of pyridine is added 0.062 part of benzyl chloride, and the mixture is kept standing at room temperature overnight. Then the pyridine is distilled off under reduced pressure, and resultant residue is chromatographed over silica gel. Ethyl actate eluates give $N_1$-(morpholinocarbonylmethyl)-$N_4$-(2-monobenzoylaminobenzyl)piperazine as oily substance.

NMR(in CDCl$_3$) ppm: 2.40(4H, singlet), 2.80(4H, singlet), 3.30, 3.18(each 1H, broad singlet), 3.53(2H, singlet), 3.60 (8H, broad, singlet), 6.8 to 8.3(9H, multiplet).

(2) According to a similar manner to that of the above Example (1), following compounds are produced from the corresponding 2-aminobenzyl piperazine derivatives and the acylating agent;

$N_1$-(morpholinocarbonylmethyl)-$N_4$-(2-diacetylaminobenzyl)piperazine, oily substance, NMR (in $CDCl_3$) ppm; 2.26(6H, singlet), 2.40(4H, singlet), 2.80(4H, singlet), 3.13, 3.23(each 1H, broad singlet), 3.60(8H, singlet), 6.8 to 7.5(4H, multiplet); $N_1$-acetyl-$N_4$-(2-diacetylaminobenzyl)piperazine, oily substance, NMR (in $CDCl_3$) ppm; 2.03(3H, singlet), 2.26(6H, singlet), 2.40(4H, multiplet), 3.46 (2H, multiplet), 3.23(2H, singlet), 6.7 to 7.4(4H, singlet);

form layer is dried over anhydrous sodium sulfate and the chloroform is distilled off. The residual oily substance is treated with 18% ethanolic hydrochloric acid and the resultant crystalline product is recrystallized from methanol to give $N_1$-methyl-$N_4$-(2-amino-3,5-dibromobenzyl)piperazine hydrochloride as pale yellow crystals melting at 182° to 185° C.

Elemental analysis: Calculated for $C_{12}H_{17}N_3Br_2 \cdot HCl \cdot H_2O$: C, 34.51; H, 4.82; N, 10.06. Found: C, 34.42, H, 5.31; N, 9.75.

EXAMPLE 2

According to a similar manner to that of Example 1, the following compounds are obtained from the corresponding aminobenzylpiperazine derivatives;

| | Starting compound | Product | Melting point (° C) |
|---|---|---|---|
| 2-1 | $N_1$-hydro-$N_4$-(2-aminobenzyl)piperazine | $N_1$-hydro-$N_4$-(2-amino-3,5-dibromobenzyl)piperazine hydrochloride | 194 to 196 |
| 2-2 | $N_1$-n-propyl-$N_4$-(2-aminobenzyl)piperazine hydrochloride | $N_1$-n-propyl-$N_4$-(2-amino-3,5-dibromobenzyl)piperazine hydrochloride | 167 to 169 |
| 2-3 | $N_1$-benzyl-$N_4$-(2-aminobenzyl)piperazine | $N_1$-benzyl-$N_4$-(2-amino-3,5-dibromobenzyl)piperazine hydrochloride | 215 to 220 |
| 2-4 | $N_1$[(morpholinocarbonyl)methyl]-$N_4$-(2-aminobenzyl)piperazine | $N_1$-[(morpholinocarbonyl)methyl]-$N_4$-(2-amino-3,5-dibromobenzyl)piperazine hydrobromide | 201 to 204 |
| 2-5 | $N_1$-($\beta$-hydroxyethyl)-$N_4$-(2-aminobenzyl)piperazine | $N_1$-($\beta$-hydroxyethyl)-$N_4$-(2-amino-3,5-dibromobenzyl)piperazine hydrochloride | 148 to 150 |
| 2-6 | $N_1$-cinnamyl-$N_4$-(2-aminobenzyl)piperazine | $N_1$-cinnamyl-$N_4$-(2-amino-3,5-dibromobenzyl)piperazine hydrochloride | 208 to 210 (decomposition) |
| 2-7 | $N_1$-isopropyl-$N_4$-(2-aminobenzyl)piperazine | $N_1$-isopropyl-$N_4$-(2-amino-3,5-dibromobenzyl)piperazine hydrochloride | 205 to 209 |
| 2-8 | $N_1$(morpholinomethylcarbonyl)-$N_4$-(2-aminobenzyl)piperazine | $N_1$-[(morpholinomethyl)carbonyl]$N_4$-(2-amino-3,5-dibromobenzyl)piperazine hydrochloride | 224 to 227 |
| 2-9 | $N_1$-(mercaptoacetyl)-$N_4$-(2-aminobenzyl)piperazine | $N_1$-mercaptoacetyl-$N_4$-(2-amino-3,5-dibromobenzyl)piperazine hydrochloride | 182 to 186 (decomposition) |
| 2-10 | $N_1$-(aminocarbonylmethyl)-$N_4$-(2-aminobenzyl)piperazine | $N_1$-(aminocarbonylmethyl)-$N_4$-(2-amino-3,5-dibromobenzyl)piperazine hydrobromide | 277 to 279 |
| 2-11 | $N_1$-(diethylaminocarbonylmethyl)-$N_4$-(2-aminobenzyl)piperazine | $N_1$-(diethylaminocarbonylmethyl)-$N_4$-(2-amino-3,5-dibromobenzyl)piperazine hydrobromide | 175 to 177 (decomposition) |
| 2-12 | $N_1$-(piperidinocarbonylmethyl)-$N_4$-(2-aminobenzyl)piperazine | $N_1$-(piperidinocarbonylmethyl)-$N_4$-(2-amino-3,5-dibromobenzyl)piperazine hydrochloride | 162 to 164 |
| 2-13 | $N_1$-(isopropylaminocarbonylmethyl)-$N_4$-(2-aminobenzyl)piperazine | $N_1$-(isopropylaminocarbonylmethyl-$N_4$-(2-amino-3,5-dibromobenzyl)piperazine hydrobromide | 155 to 157 (decomposition) |
| 2-14 | $N_1$-(N-methyl-N-cyclohexylaminocarbonylmethyl)-$N_4$-(2-aminobenzyl)piperazine | $N_1$-(N-methyl-N-cyclohexylaminocarbonylmethyl)-$N_4$-(2-amino-3,5-dibromobenzyl)piperazine hydrochloride | 155 to 159 (decomposition) |
| 2-15 | $N_1$-aminocarbonyl-$N_4$-(2-aminobenzyl)piperazine | $N_1$-aminocarbonyl-$N_4$-(2-amino-3,5-dibromobenzyl)piperazine hydrochloride | 165 to 168 (decomposition) |
| 2-16 | $N_1$-(morpholinocarbonylmethyl)-$N_4$-(2-diacetylaminobenzyl)piperazine | $N_1$-(morpholinocarbonylmethyl)-$N_4$-(2-diacetylamino-3,5-dibromobenzyl)piperazine hydrochloride | 163 to 165 |
| 2-17 | $N_1$-(morpholinocarbonylmethyl)-$N_4$-(2-monobenzoylaminobenzyl)piperazine | $N_1$-(morpholinocarbonylmethyl)-$N_4$-(2-monobenzoylamino-3,5-dibromobenzyl)piperazine hydrochloride | 162 to 164 |
| 2-18 | $N_1$-acetyl-$N_4$-(2-diacetylaminobenzyl)piperazine | $N_1$-acetyl-$N_4$-(2-diacetylamino-3,5-dibromobenzyl)piperazine hydrochloride | 140 to 143 |
| 2-19 | $N_1$-benzoyl-$N_4$-(2-benzoylaminobenzyl)piperazine | $N_1$-benzoyl-$N_4$-(2-monobenzoylamino-3,5-dibromobenzyl)piperazine hydrochloride | 153 to 155 |

$N_1$-benzoyl-$N_4$-(2-monobenzoylaminobenzyl)piperazine, oily substance, NMR (in $CDCl_3$) ppm: 2.2 to 2.6(4H, multiplet), 3.3 to 3.8(4H, multiplet), 3.41(2H, singlet), 6.8 to 8.4 (14H, multiplet).

EXAMPLE 1

$N_1$-methyl-$N_4$-(2-amino-3,5-dibromobenzyl)piperazine hydrochloride

In 10 volume parts of acetic acid is dissolved 0.810 part of $N_1$-methyl-$N_4$-(2-aminobenzyl)piperazine and, under vigorous stirring, 0.320 part of bromine is added at room temperature. After 30 minutes of reaction, the solvent is distilled off under reduced pressure and the residue is made alkaline with concentrated aqueous ammonia and extracted with chloroform. The chloro-

EXAMPLE 3

To a solution of 1.66 parts of $N_1$-(morpholinocarbonylethyl)-$N_4$-(2-aminobenzyl)piperazine in 50 volume parts acetic acid is added 14 g. of 10% chlorine acetic acid solution under ice-cooling, followed by stirring at room temperature for 4 hours. Then, acetic acid is distilled off under reduced pressure, and the residue is made alkaline with 10% aqueous solution of sodium hydroxide. The mixture is extracted with chloroform, and the chloroform layer is dried over sodium sulfate. The chloroform is distilled off, and the residue is chromatographed over alumina. Ethyl acetate eluates give oily substance. The resultant oily substance is treated with ethanolic hydrochloric acid, and recrystallization of the resultant from ethanol-isopropyl ether gives $N_1$-(morpholinocarbonylethyl)-$N_4$-(2-amino-3,5-dichlorobenzyl)-piperazine hydrochloride as pale yellow crystals melting at 150° to 154° C (decomposition).

Elemental analysis: Calculated for $C_{18}H_{26}N_4O_2Cl_2\cdot2HCl\cdot\frac{1}{2}H_2O$: C, 44.73; H, 5.63; N, 11.59. Found: C, 44.27; H, 6.00; N, 11.19.

EXAMPLE 4

(1) A mixture of 0.56 part of 2-amino-3,5-dibromobenzylalcohol, 1.0 part of N-methyl piperazine and 2 parts of propionic acid is heated at 140° C for 8 hours under stirring. Then, the propionic acid is distilled off under reduced pressure. The residue is extracted with chloroform. The chloroform layer is washed with water and dried over sodium sulfate. Evaporation of the solvent gives oily residue. The residue is chromotographed over silica gel. Ethyl acetate eluates are treated with ethanolic hydrochloric acid. This procedure gives $N_1$-methyl-$N_4$-(2-amino-3,5-dibromobenzyl)piperazine hydrochloride melting at 182° to 185° C.

(2) According to a similar manner to that of the above Example (1), the following compounds are produced from the corresponding piperazine derivatives;

$N_1$-($\beta$-hydroxyethyl)-$N_4$-(2-amino-3,5-dibromobenzyl)piperazine hydrochloride melting at 148° to 150° C; $N_1$-n-propyl-$N_4$-(2-amino-3,5-dibromobenzyl)piperazine hydrochloride melting at 167° to 169° C; $N_1$-isopropyl-$N_4$-(2-amino-3,5-dibromobenzyl)piperazine hydrochloride melting at 205° to 209° C; $N_1$-benzyl-$N_4$-(2-amino-3,5-dibromobenzyl)piperazine hydrochloride melting at 215° to 220° C.

EXAMPLE 5

(1) To a solution of 0.423 part of $N_1$-(morpholinocarbonylmethyl)-$N_4$-(2-amino-3,5-dibromobenzyl)piperazine in 4 volume parts of pyridine is added 0.25 part of benzoylchloride, and the mixture is kept standing overnight at room temperature. The solvent is distilled off, and residue is chromatographed over alumina. Ethyl acetate eluates gives oily substance. The resultant oily substance is treated with ethanolic hydrochloric acid, and to the resultant is added isopropyl ether to give $N_1$-morpholinocarbonylmethyl-$N_4$-(2-monobenzoylamino-3,5-dibromobenzyl)piperazine hydrochloride melting at 162° to 164° C.

(2) According to a similar manner to that of the above Example (1), the following compound is produced from the corresponding acylating agent; $N_1$-acetyl-$N_4$-(2-diacetylamino-3,5-dibromobenzyl)piperidine hydrochloride melting at 140° to 143° C.

EXAMPLE 6

(1) To a solution of 0.35 part of $N_1$-hydro-$N_4$-(2-amino-3,5-dibromobenzyl)piperazine in 5 volume parts of dimethylformamide are add 0.2 part of triethylamine and 0.149 part of morpholinocarbonylmethyl chloride, and the mixture is heated at 100° C for 2 hours. The solvent is distilled off under reduced pressure, and the residue is extracted with chloroform. The chloroform layer is dried over sodium sulfate. The chloroform is distilled off and the residue is treated with ethanolic hydrobromic acid to give $N_1$-(morpholinocarbonylmethyl)-$N_4$-(2-amino-3,5-dibromobenzyl)piperazine hydrobromide melting at 201° to 204° C.

(2) According to a similar manner to that of the above Example (1), the following compounds are produced from the corresponding piperazine derivatives and halides;

$N_1$-methyl-$N_4$-(2-amino-3,5-dibromobenzyl)piperazine hydrochloride melting at 182° to 185° C $N_1$-($\beta$-hydroxyethyl)-$N_4$-(2-amino-3,5-dibromobenzyl)piperazine hydrochloride melting at 148° to 150° C $N_1$-isopropyl-$N_4$-(2-amino-3,5-dibromobenzyl)piperazine hydrochloride melting at 205° to 209° C $N_1$-n-propyl-$N_4$-(2-amino-3,5-dibromobenzyl)piperazine hydrochloride melting at 167° to 169° C $N_1$-[(morpholinomethyl)carbonyl]-$N_4$-(2-amino-3,5-dibromobenzyl)piperazine hydrochloride melting at 224° to 227° C.

What is claimed is:

1. A compound of the formula

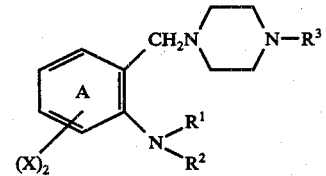

wherein $R^1$ and $R^2$ are the same or different and each stands for a hydrogen atom, alkylcarbonyl, whose alkyl moiety is of 1 to 3 carbon atoms, or benzoyl; $R^3$ stands for straight-chain or branched alkyl having 1 to 6 carbon atoms which is substituted by amino-carbonyl represented by the formula

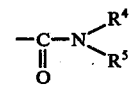

wherein $R^4$ and $R^5$ form a morpholino ring together with the nitrogen atom adjacent thereto, and X stands for a halogen atom, and a pharmaceutically acceptable acid addition salt thereof.

2. A compound as claimed in claim 1, wherein the compound is that having the halogen atoms at 3- and 5-positions of the ring A.

3. A compound as claimed in claim 2, wherein both of the halogen atoms are bromine.

4. A compound as claimed in claim 2, wherein both of $R^1$ and $R^2$ are hydrogen.

5. A compound as claimed in claim 2, wherein both of $R^1$ and $R^2$ are alkylcarbonyl, whose alkyl moiety is of 1 to 3 carbon atoms.

6. A compound as claimed in claim 2, wherein one of $R^1$ and $R^2$ is benzoyl and the other is hydrogen.

7. A compound as claimed in claim 1, wherein the compound is $N_1$-(morpholinocarbonylmethyl)-$N_4$-(2-amino-3,5-dibromobenzyl)piperazine.

8. A compound as claimed in claim 1, wherein the compound is $N_1$-(morpholinocarbonylmethyl)-$N_4$-2-(2-diacetylamino-3,5-dibromobenzyl)piperazine.

9. A compound as claimed in claim 1, wherein the compound is $N_1$-(morpholinocarbonymethyl)-$N_4$-(2-monobenzoylamino-3,5-dibromobenzyl)piperazine.

10. A compound as claimed in claim 1, wherein the compound is $N_1$-(morpholinocarbonylethyl)-$N_4$-(2-amino-3,5-dichlorobenzyl)piperazine.

* * * * *